United States Patent [19]

Gergely et al.

[11] Patent Number: 4,832,956

[45] Date of Patent: May 23, 1989

[54] DISINTEGRATING TABLET AND PROCESS FOR ITS PREPARATION

[76] Inventors: Gerhard Gergely; Thomas Gergely; Irmgard Gergely, all of Gartengasse 8, Vienna, A-1050, Austria

[21] Appl. No.: 56,478

[22] PCT Filed: Sep. 20, 1986

[86] PCT No.: PCT/EP86/00551

§ 371 Date: May 19, 1987

§ 102(e) Date: May 19, 1987

[87] PCT Pub. No.: WO87/01936

PCT Pub. Date: Apr. 9, 1987

[30] Foreign Application Priority Data

Sep. 25, 1985 [CH] Switzerland ............ 4153/85-8

[51] Int. Cl.$^4$ ............................................ A61K 9/46
[52] U.S. Cl. ................................. 424/466; 424/479; 424/480; 424/482; 424/468; 427/3
[58] Field of Search ............. 424/466, 469, 80, 468, 424/479, 480, 482; 427/3

[56] References Cited

U.S. PATENT DOCUMENTS

| | | | |
|---|---|---|---|
| 4,127,645 | 11/1978 | Witzel et al. | 424/466 X |
| 4,289,751 | 9/1981 | Windheuser | 424/44 X |
| 4,539,198 | 9/1985 | Powell et al. | 424/465 X |
| 4,678,661 | 7/1987 | Gargely et al. | 424/44 |
| 4,687,662 | 8/1987 | Schobel | 424/44 |
| 4,728,513 | 3/1988 | Ventouras | 424/480 X |

FOREIGN PATENT DOCUMENTS

| | | |
|---|---|---|
| 0052076 | 5/1982 | European Pat. Off. . |
| 2416903 | 10/1975 | Fed. Rep. of Germany . |
| 2383659 | 10/1978 | France . |
| 2552308 | 3/1985 | France . |
| 825892 | 12/1959 | United Kingdom . |
| 974917 | 11/1964 | United Kingdom . |

*Primary Examiner*—Michael Lusignan
*Attorney, Agent, or Firm*—Marmorek, Guttman & Rubenstein

[57] ABSTRACT

A desintegration tablet contains the filler material in a form and/or size which when coming in contact with water at ambient temperature dissolves so slowly that the water absorption and the action of the desintegration agent are not affected. The grains are either coated with a layer of slowly dissolving substance, in particular a colloid or pseudo-colloid, or consist of a crushed melted substance having a grain size preferably of between 0.2 and 0.6 mm, e.g. mannitol, sorbital and/or xylitol.

19 Claims, No Drawings

DISINTEGRATING TABLET AND PROCESS FOR ITS PREPARATION

The invention relates to a tablet which contains at least one slowly dissolving or sparingly soluble pharmaceutical active compound and at least one disintegrating agent, and to a particular form of the tablet, and finally to a process for its preparation. A tablet of this type is disclosed in, for example, EP-A-No. 52,076 or GB-C-No. 825,892.

Compacts compressed to form solid articles, as are usual in powder technology, should be hard and mechanically stable in many cases but nevertheless disintegrate into the tablet components within a short time in water in order to release the active compounds and to permit them to come into contact with water or with body fluid.

Since the existence of compressed tablets, a very wide variety of substances have been incorporated for this purpose, in order to cause the disintegration of such substances. The substance first used, and the traditional one, was starch. Today, there are a large number of substances which are used for the disintegration of tablets, such as, for example, finely disperse silica, microcellulose or, in particular, polyvinylpyrrolidone, which undoubtedly has the best disintegrating effect. However, the mechanical efficiency of all these disintegrating agents depends to a great extent on the water solubility of the ingredients of the compressed tablet. Paradoxically, the higher the water solubility of the ingredients or accompanying substances, the more difficult becomes the choice of a suitable disintegrating agent and the slower and more unreliable becomes the disintegration of such compressed tablets. This may be due to the fact that the concentrated and therefore often highly viscous (e.g. sugar) solution of such substances which forms at the surface of the compressed tablet immediately closes and blocks the capillaries of the disintegrating agent.

Although the mode of action of such disintegrating agents was previously attributed to their swelling action, the more prevalent opinion today is that capillary forces acting on the particles of the disintegrating agent reduce the binding forces at certain points in the tablet and cause disintegration. Nevertheless, it is probable that, in addition to the capillary action, an increase in volume is necessary for tablet disintegration, so that a plurality of concurrent factors is involved. However, the capillary activity, which is scarcely measurable, is adversely affected by a very large number of factors during production of the preparations or pressing of the tablets. These are, in particular, high compressive pressures, granulation assistants, etc., which close the capillaries and thus reduce the disintegrating effect.

For this reason and other reasons, it has been virtually impossible to date to effect rapid disintegration of tablets containing large amounts of water-soluble carbohydrates. On the other hand, modern pharmaceutical technology requires tablets which both are pleasant to take orally and disintegrate rapidly in water, their constituents either dissolving or at least remaining dispersed and giving a drink. However, the tablets according to the two prior art Patents mentioned at the outset do not meet this requirement. It has in fact been virtually impossible to date to find, as an administration form, an intermediate product between the normal tablet or capsule, which either is swallowed or merely disintegrates in water, and an effervescent tablet which dissolves and gives a pleasant-tasting drink. It is therefore the object of the present invention to provide a novel tablet which, when taken as such, can be chewed or sucked and also disintegrates in water in the course of 30 to 60 seconds and gives a pleasant-tasting suspension or solution. A further object of the invention is to make the tablet glucose-free and sucrose-free and, if necessary, to be able to dispense with the use of effervescent additives.

As a rule, all substances are divided into readily soluble substances and substances which are difficult to dissolve; this phraseology is inexact because what is actually meant by this is "highly" and "slightly" soluble. Whether a substance which can be dissolved in a relatively large amount in, for example, one liter of water dissolves rapidly ("readily") or slowly ("with difficulty") makes a great deal of difference. This difference, to which too little importance has obviously been attached in the past, is utilized by the invention.

There is even a further stage to be taken into account. Conventional sucrose grains are, for example, rapidly dissolved at the surface, forming a concentrated sugar solution which allows further dissolution of the grains to take place only slowly, unless it is distributed by, for example, stirring. On the other hand, in the case of a substance such as, for example, fused mannitol (see below), which is dissolved more slowly at the surface, such a concentrated solution is not formed; the dissolved molecules can diffuse away more rapidly, and complete dissolution of the grain may then take place more rapidly than in the case of sucrose.

If in fact the process of tablet disintegration is considered more exactly, the time-dependence of the processes obviously plays a great role. Regardless of whether a swelling action or a capillary action is involved, the disintegration assistant must certainly first be wet and thoroughly penetrated by the water before the accompanying substances begin to go into solution. If in fact the accompanying substances were to dissolve more rapidly or at least at the same time and to the same extent, the reduction in volume which occurs as a result of the dissolution of the accompanying substances would prevent disintegration of the tablet or reduce the efficiency of the disintegrating agent. Furthermore, water-soluble substances tend to exhibit binder properties during the dissolution process and, as mentioned, prevent disintegration even in the case of capillary substances.

It has therefore been very difficult to date to convert, for example, carbohydrates into rapidly disintegrating tablet forms, since the dissolution of the readily water-soluble carbohydrates in the said forms has an adverse effect on the efficiency of virtually all disintegrating agents. However, a tablet of this type has now been provided by the measures of the characterizing clause of claim 1.

Tee filler particles may be particularly coarse crystals (for example 0.2 to 0.6 mm particle size) or other crystal modifications which dissolve more slowly than fine crystals or than the conventional powders. It is also possible to coat the particles of readily soluble substances—for example by conventional vacuum technology—with a very thin layer of a pharmaceutically acceptable, slowly dissolving material, for example with a colloid or pseudocolloid or the like. It is important in every case that the water first reaches the particles of the disintegrating agents present in the pressed tablet mixture and causes these particles to swell and hence to disintegrate the tablet before any rapidly dissolving active compounds or fillers are dissolved by the water; the highly concentrated solution which then forms at the particle surfaces cannot penetrate the capillaries of the disintegrating agent.

However, care should also be taken to ensure that the colloids, which may swell rapidly, do not coat the parts of disintegrating agent projecting from the particle surface with an impenetrable gel before the disintegrating agent can begin to be effective.

Advantageous further embodiments of the tablet according to the invention are described in claims 2 to 9, and a process for the preparation of the tablets according to the invention is described in claim 10.

In a particularly preferred embodiment of the present invention, it is therefore envisaged that the rapidly dissolving filler is rendered slow-dissolving by melting, cooling and milling. This has two additional advantages:

On the one hand, the surface is frequently provided with an irregular, partially amorphous or microcrystalline structure (in contrast to the smooth, hard crystal faces), with the result that the mixtures can be much more easily pressed to tablets, frequently even without the addition of a binder ("direct pressing material"); conventional crystalline granules alone are virtually impossible to press and in fact always require a binder. However, the addition of a binder often implies an additional operation during manufacture.

On the other hand, the disintegrating agent can be introduced directly into the melt so that, after cooling and milling, free disintegrating agent residues are present at the grain fracture surfaces and project into the interior of the grains. The contact surface formed during tablet pressing between the individual grains is interrupted by the particles of disintegrating agent exposed at the surface. If water enters between the grains, the particles of disintegrating agent immediately swell and separate the grains; the latter become more rapidly soluble because the particles of disintegrating agent projecting into the interior of the particular grain swell and disintegrate the grains into smaller particles. The active compounds are released at the same time and go into solution or suspension.

Hence, the grains should not be packed too tightly in the tablet, so that water can penetrate into the pores between the grains. Particularly where, without the addition of a binder, the bond between he grains is a purely electrical-mechanical one, it is easier to break than a colloid bond.

A particularly impressive example of this is mannitol. Whereas powdered mannitol, as available commercially, dissolves very readily and rapidly in water, mannitol can be rendered slow-dissolving by melting it, rapidly cooling the melt and then milling it in special mills, for example to particle sizes between 0.2 and 0.6 mm. It is obvious that, because of the larger surface area alone, normal mannitol, which has a particle size of the order of magnitude of 10 micron, will dissolve more rapidly than fused mannitol which, because of its compact physical structure and the smaller surface area of the fused particles, will dissolve just as readily, but more slowly, in water.

It is of course also important that there is no need to add magnesium stearate as a lubricant during pressing of binder-free grains of fused mannitol to give a tablet; magnesium stearate would render the surface of the tablet hydrophobic and have an extremely retarding effect on tablet disintegration during subsequent contact with water.

The rate of dissolution of a substance such as mannitol can now be even further reduced in a very elegant manner, this being achieved (paradoxically) by adding a disintegrating agent. For this purpose, for example, 10-20% of very pure microcellulose are added to the molten mannitol. This microcellulose is introduced into the molten mannitol using a very efficient stirrer, and the mannitol is then quenched and milled. The microcellulose particles are held on or in the mannitol, with the result that the fused mannitol is more compact and therefore more slowly soluble. If such particles are pressed to form a tablet with the possible addition of a further disintegrating agent, in the presence of water swelling of the disintegrating agent present at the boundary would take place more rapidly than surface dissolution or dissolution of the mannitol, which has been rendered more compact and therefore rather slowly soluble as a result of the melting process. Consequently, the tablet begins to disintegrate immediately, the mannitol particles first dispersing in water and only dissolving afterward. A large number of active compounds can be incorporated into a tablet of this type, the said active compounds likewise either dissolving or going into suspension in water; in this way, disintegration rates of 30 to 60 seconds are achieved even in the case of readily water-soluble fillers, but the tablets can be pressed to great hardness of, for example, 10 to 15 kp.

It is true that active compounds have been sprayed in molten form in the past (for example DE-A-No. 2,116,903) in order to make them more readily tabletable. According to FR-A-No. 2,383,659, various polysaccharides mixed with an oxygen-sensitive active compound are compressed by heating to 80° C., although in actual fact the polysaccharides do not melt; the product is then comminuted again and the shelf life of the active compound thus improved. Furthermore, various auxiliaries, such as, for example, flavors, artificial sweeteners, thickeners or binders, antiadhesive agents or lubricants, etc. were added, but not slow-dissolving fillers, such as those which have the advantages according to the invention. According to the invention, however, it has been found that not more than one third, preferably not more than 20%, of the total amount of the tablet may consist of the stated auxiliaries, some of which may dissolve relatively rapidly in water.

The novel disintegration principle is of great importance in the composition of new systems of compressed materials which have a dual use. Such compressed materials can, if desired, be caused to disintegrate in a relatively very small amount of water, a suspension of the tablet ingredients being formed in the course of 30 to 60 seconds; however, they can also be swallowed, chewed or sucked.

The effect is also noteworthy because a tablet of this type exhibits very different behavior in the mouth. Here, because of the small amount of moisture provided by the saliva, the tablet does not disintegrate but behaves like a normal chewable or sucking tablet which is pleasant to take.

The advantage of the system is that firstly it is cheap to use and produce and in particular permits any variation in taste. The crosslinked polyvinylpyrrolidones which have been widely used recently and permit the formation of similar systems have the disadvantage of a high price and a sandy taste which is very disturbing when the tablet is taken. Furthermore, such crosslinked polyvinylpyrrolidones fail in the presence of readily (rapidly) soluble substances.

The process described above can be varied very widely. Many carbohydrates (and incidentally also a very large number of active compounds) can be melted without decomposition and mixed with disintegrating agents. The melt is then allowed to solidify and is milled to the desired particle size optimum for pressing to give the relevant tablets. In general, a few preliminary experiments are sufficient for finding a suitable model for a desired system.

It is obvious that this system can be used to produce a large number of disintegrating tablets since virtually all disintegrating agents used to date for the disintegration of tablets can, provided that they are thermally stable, be incorporated into the melt of carbohydrates. Moreover, the dissolution characteristics of such systems are relatively insensitive to sweeteners and flavors and the said systems can therefore be used for the production of pleasant-tasting products.

It should also be emphasised that, because of the smaller surface area and the greater compactness (tightness) of the granules of the fused material, such systems are substantially less moisture-sensitive than normal disintegrating tablets. This is of course because normal atmospheric humidity too can act to a lesser extent on the smaller surface area of the compressed fused material than on compressed particles of smaller size.

The fillers according to the invention which contain disintegrating agents can also be very advantageously used for the production of the noneffervescent layer of multilayer effervescent tablets. In modern medicine, greater and greater efforts are being made to incorporate pharmaceutical active compounds into effervescent tablets because the oral administration of tablets, particularly where high doses are involved, presents difficulties for many patients, whereas effervescent lemonades are readily drunk; furthermore, it is possible in this way to ensure the additional intake of a sufficient amount of water, which is desirable per se.

Unfortunately, it has been found that various active compounds are unstable or have only limited stability alongside one another and/or in effervescent mixtures. It has therefore also been proposed that a multilayer tablet be provided, in which the effervescent mixture and/or an active compound are present in one layer, and the other active compound or compounds are present in another layer. In many cases, however, this solution is not feasible because the active compounds present in the other layer, particularly in the pressed form, do not dissolve so rapidly in water as the effervescent mixture.

If the layer which is free of the effervescent agent is produced according to the invention, the wick action of the disintegrating agent causes the water also to penetrate and disintegrate the tablet layer which does not contain any effervescent mixture in the time taken for the effervescent layer to dissolve.

If it is desired to introduce, for example, acetylsalicylic acid into a low-sodium effervescent tablet, this is difficult because it is hydrolysed to a greater extent under the action of the more strongly alkaline calcium carbonate. It is possible, for example, to incorporate the effervescent mixture in one layer and the acetylsalicylic acid in the other layer free of effervescent agent; however, this is only useful if this latter layer has the composition according to the invention. Otherwise, there is the danger that disintegration of the layer which is free of effervescent agent would not take place as rapidly as dissolution of the layer containing effervescent agent, and the former layer would therefore remain as an individual tablet, while the first layer would become detached from this second layer during effervescence. Furthermore, the acetylsalicylic acid requires carbonic acid in order to dissolve, since it is hydrophobic and therefore relatively sparingly soluble.

In this case, it is particularly expedient for the layer which is free of effervescent agent to be covered on both sides by a layer containing an effervescent mixture, since then carbonic acid will in any case be formed underneath the layer which is free of effervescent agent, providing an additional "stirring effect" for the disintegration and dissolution of the middle layer which is free of an effervescent agent but contains a disintegrating agent. Where an effervescent layer is present only on one side, this layer always "floats" on the surface and there is no stirring effect for the layer which is free of effervescent agent and is suspended underneath.

EXAMPLE 1

90 parts of mannitol are melted at 180° C. in an oil bath; 10 parts of microcellulose are suspended in the melt using a highly efficient stirrer. The melt is poured onto cooled cups, where it immediately solidifies. The material is comminuted by means of a cutting mill. Particles between 0.2 and 0.6 mm are preferably used. 200 mg of erythromycin succinate and a further 50 mg of microcellulose are then added to 400 mg of this mannitol/cellulose melt, and the mixture is tableted without the further addition of a binder. The tablet has a hardness of about 10 kg with a punch or 12 mm diameter and disintegrates in water in the course of 15–30 seconds. The addition of flavors and sweeteners does not change the disintegration rate and the properties of the tablet.

EXAMPLE 2

200 mg of penicillin V are pressed with 300 mg of the mannitol/cellulose product from Example 1, 50 mg of starch and 30 mg of fumaric acid, as well as with conventional flavors and sweeteners. The hardness of the tablet is 10 kg and the disintegration time 20–30 seconds.

EXAMPLE 3

Starch can also be incorporated particularly advantageously into the mannitol melt. 92 parts of mannitol are melted at 180° C.; 8 parts of potato starch are then introduced slowly, and suspended by stirring. This has the further advantage that the water present in the starch evaporates, with the result that the starch dries and becomes an extremely effective disintegrating agent. The melt is cooled again, and the solidified melt is milled to particles between 0.2 and 0.5 mm.

This system can be used principally for processing hydrophobic products, such as, for example, vitamin E adsorbates. For example, 400 mg of 50% vitamin E adsorbate on gelatine and 1000 mg of the mannitol/starch product are pressed together with flavors and sweeteners to give a tablet The hardness of the tablet is 8 kg, and the disintegration time 20 seconds.

EXAMPLE 4

90 parts of anhydrous citric acid are melted at 150° C.; 10 parts of finely disperse silica are introduced into the melt, and the melt is quenched. The product obtained is milled to a particle size of 0.2 to 0.5 mm.

This product can be used to produce disintegrating tablets which consist of, for example, 3 parts of the mannitol/cellulose melt from Example 1, 1 part of the above-mentioned citric acid/silica melt and 1 part of vitamin C, as well as 0.2 part of microcellulose.

The mixture is pressed to tablets, which disintegrate into their constituents in the course of 30 to 45 seconds. If the readily (rapidly) soluble citric acid were to be used in the non-fused form, tablet disintegration would be very much slower.

EXAMPLE 5

Adipic acid too can be treated similarly to citric acid, and both cellulose and Aeoosil can be added, in a proportion of 10 to 20%, to the melt. If a microcellulose-containing melt with these constituents is quenched and milled to a particle size of 0.2 to 0.5 mm, it is just as suitable as citric acid for acidifying readily disintegrating instant tablets.

EXAMPLE 6

Pharmaceutical active compounds too can be treated in a similar manner.

80 parts of cyclandelate are heated to 60° C., and 20 parts of microcellulose are introduced into the melt. The product is cooled to −50° C. and milled to a particle size of about 0.5 mm in cooled mills.

If such milled material mixed with 20 to 30% of starch is milled, tablets which immediately disintegrate in water are obtained, the cyclandelate released being dispersed in very fine form because the microcellulose present in the fused grains disintegrates it further.

EXAMPLE 7

60 parts of xylitol are stirred with 40 parts of starch at 160° C., and the mixture is quenched. The material obtained is milled to particles of 0.2 to 0.5 mm and, with the addition of a further 10 to 20% of starch and conventional active compounds, flavors and/or sweeteners, gives hard tablets which disintegrate in a period of 30–40 seconds, provided that the active compounds, flavors or sweeteners do not dissolve rapidly.

We claim:

1. A tablet comprising at least one slowly or sparingly soluble pharmaceutically active compound, an effective amount of at least one disintegrating agent which disintegrates upon contact with water, and the balance comprising primarily at lest one soluble filler in a form which renders it more slowly soluble on contact with water than the disintegrating action of said disintegrating agent.

2. A tablet as claimed in claim 1, wherein the filler comprises a melt which has been comminuted into filler particles having a size of about 0.1 to 0.6 mm.

3. A tablet as claimed in claim 2, wherein the filler particles comprise at least one of the substances mannitol, orbitol and xylitol.

4. A tablet as claimed in claim 2, wherein the filler particles comprise at least one of the substances citric acid and adipic acid.

5. A tablet as claimed in claim 2, wherein the filler particles incorporate therein at least one pharmaceutically active compound.

6. A tablet as claimed in claim 2, the filler particles incorporate therein at least one disintegrating agent.

7. A tablet as claimed in claim 2, wherein the filler particles incorporate therein at least one material selected from the group consisting of another type of filler, a disintegrating agent, a pharmaceutically active compound and an auxiliary compound.

8. A tablet as claimed in claim 2, wherein, in addition to the active compound, the disintegrating agent and the filler, the tablet further comprises about 20% to about 33⅓% by weight of readily soluble auxiliaries based on the total amount.

9. A multilayer tablet comprising at least one layer having a composition according to claim 2 wherein said tablet further comprises an effervescent layer.

10. A tablet as claimed in claim 2 wherein said filler comprises a carbohydrate.

11. A tablet as claimed in claim 2 wherein said disintegrating agent is selected from the group consisting of starch, silica, microcellulose, and polyvinylpyrrolidone.

12. A tablet as claimed in claim 1, wherein the filler comprises a melt.

13. The tablet of claim 2, wherein said melt has been comminuted into filler particles of a predetermined size.

14. A tablet as claimed in claim 3, wherein said filler particles have a size of about 0.1 to 0.6 nm.

15. A tablet as claimed in claim 1, wherein said soluble filler is coated with a layer of a slow dissolving material.

16. A tablet comprising a therapeutically effective amount o at least one slowly or sparingly soluble pharmaceutically active compound, an effective amount of at least one disintegrating agent, and the balance comprising primarily granules of a fused filler material, said filler material being selected from the group consisting of mannitol, sorbitol, xylitol, and combinations thereof, said disintegrating agent being dispersed within said granules.

17. A process for the preparation of a tablet, comprising melting a filler material, dispersing an effective amount of at least one disintegrating agent in said melt, cooling said melt, comminuting said cooled melt into granules of a predetermined particle size, admixing a therapeutically effective amount of a slowly or sparingly soluble pharmaceutically active compound with said granules, and pressing said mixture into tablet form.

18. Process as claimed in claim 17, wherein at least one compound selected from the group consisting of another type of disintegrating agent, a pharmaceutically active compound and an auxiliary compound is also dispersed in the melt.

19. Process as claimed in claim 17, wherein at least one compound selected from the group consisting of a pharmaceutically active compound, an auxiliary compound and another type of disintegrating agent is admixed to said particles before pressing into a tablet.

* * * * *